United States Patent [19]

Fajula et al.

[11] Patent Number: 5,534,239
[45] Date of Patent: Jul. 9, 1996

[54] PROCESS FOR THE SYNTHESIS OF A SILICA ENRICHED CRYSTALLINE ALUMINOSILICATE HAVING THE OFFRETITE STRUCTURE, THE ALUMINOSILICATE OBTAINED AND ITS USE AS A CATALYST FOR THE CONVERSION OF HYDROCARBONS

[75] Inventors: François Fajula, Theyran; Joel Patarin, Mulhouse; Thierry Des Courieres; Fredj Fitoussi, both of Lyons, all of France

[73] Assignee: Societe Nationale Elf Aquitaine, Courbevoie, France

[21] Appl. No.: 539,507

[22] Filed: Oct. 6, 1995

Related U.S. Application Data

[63] Continuation of Ser. No. 163,590, Dec. 6, 1995, abandoned, which is a continuation of Ser. No. 893,592, Jun. 2, 1992, abandoned, which is a continuation of Ser. No. 670,975, Mar. 18, 1991, abandoned.

[30] Foreign Application Priority Data

Mar. 23, 1990 [FR] France .................................. 90 03704

[51] Int. Cl.$^6$ .................................................. C01B 39/30
[52] U.S. Cl. .................. 423/713; 423/705; 423/DIG. 38; 502/85; 502/86; 502/77

[58] Field of Search ..................... 423/700, 705, 423/713, DIG. 38; 502/77, 85, 86

[56] References Cited

U.S. PATENT DOCUMENTS

| 3,506,400 | 4/1970 | Eberly Jr. et al. . |
| 3,578,398 | 5/1971 | Jenkins . |
| 4,834,961 | 5/1989 | Fajula et al. . |
| 4,840,930 | 6/1989 | La Pierre et al. . |
| 4,994,250 | 2/1991 | Occelli . |

FOREIGN PATENT DOCUMENTS 0190949  8/1986  European Pat. Off. .

Primary Examiner—Mark L. Bell
Assistant Examiner—David Sample
Attorney, Agent, or Firm—Burgess, Ryan and Wayne

[57] ABSTRACT

Process for the synthesis of a silica-enriched crystalline aluminosilicate having the offretite structure from a nucleation gel A containing sources of silicon, aluminium, alkali metal ions, an organic structuring agent and water and a growth gel B containing sources of silicon, aluminium, alkali metal ions and water. The crystals formed are calcined, the ions are replaced by protons and the crystals are subjected to a hydrothermal treatment followed by a treatment with a strong mineral acid. The aluminosilicate formed has a good selectivity in acid catalysis reactions and is characterized by its good stability.

22 Claims, No Drawings

1

PROCESS FOR THE SYNTHESIS OF A SILICA ENRICHED CRYSTALLINE ALUMINOSILICATE HAVING THE OFFRETITE STRUCTURE, THE ALUMINOSILICATE OBTAINED AND ITS USE AS A CATALYST FOR THE CONVERSION OF HYDROCARBONS

This application is a continuation of Ser. No. 08/163,590 filed Dec. 6, 1993, now abandoned, which is a continuation of Ser. No. 07/893,592 filed Jun. 2, 1992, now abandoned, which is a continuation of Ser. No. 07/670,975, now abandoned.

BACKGROUND OF THE INVENTION

1. Field of the Invention

The present invention relates to the synthesis of a silica-enriched crystalline aluminosilicate having the offretite structure, the aluminosilicate thus obtained and its use as a catalyst in the conversion of hydrocarbons.

2. Description of the Related Art

Offretite, which was first identified by Professor GONNARD in 1890 in the Mont Simiouse basalts, was not definitively identified and distinguished from erionite until 1967 by BENNET and GARD (Nature 214 1005 (1967)).

Offretite belongs to the chabazite group and crystallizes in the hexagonal system. Its structure is made up of a stack of "cancrinite" frameworks connected by hexagonal prisms. The "cancrinite" frameworks have openings on 6 sides 0.18 nm in diameter. These stacks are connected to one another by "gmelinite" frameworks. These frameworks have openings on 8 sides, accessible to molecules having a critical diameter of about 0.5 nm. The spatial arrangement of these entities leads to a porous structure characterized by channels 0.64 nm in diameter, accessible through 12 tetrahedral openings. Offretite is thus classified amongst the zeolites in which the pore openings are of average size.

Erionite has the same stacks of cancrinite frameworks and prisms, but a rotation of 60° between two successive cancrinite frameworks causes a periodic obstruction of the channels. In some cases there is intergrowth between offretite and erionite, which adds to the difficulty in identification. Powder X-ray diffraction does not enable these two structural types to be distinguished.

However, it is possible to distinguish between these two structures by other methods, such as electron diffraction, X-ray diffraction on a monocrystal, or the measurement of the strain index (SI).

According to this latter method, developed by FRILETTE (J. CATAL. 67,218, (1981)), the relative rates of cracking of n-hexane and 3-methylpentane are compared.

The strain index (SI) is defined as being the ratio of the logarithm of the fraction of unconverted n-hexane to the logarithm of the fraction of unconverted 3-methylpentane. The test is carried out under atmospheric pressure on an equimolecular mixture. It is possible either to observe the change in the strain index as a function of time or to fix a given time, in general 20 min.

In the absence of steric strain, the strain index is low (less than 1). Steric strains associated with the structure (small-pore zeolite) or with ageing (narrowing of the pores due to coking) lead to high values. For example, erionite, because of the periodic obstruction of the channels, gives a value largely greater than 10.

One of the major uses of zeolites is acid catalysis. In fact, zeolites are aluminosilicates composed of chains of $SiO_4$ and $AlO_4^-$ tetrahedra. Electrical neutrality is ensured by compensating cations. In general these cations are $K^+$ or $Na^+$ ions replaceable by $NH_4^+$. A heat treatment enables $NH_4^+$ to be converted to $H^+$ and thus enables acid solids to be obtained.

It is well known that for each reaction catalysed by a zeolite the aluminic molar fraction m, which is defined as the atomic ratio $$\frac{Al}{Al+Si},$$

plays a fundamental role.

It directly determines the density of acid sites. A change in the aluminic fraction causes a change in the number and the strength of acid sites. This change can be obtained during the synthesis or by a post-synthesis treatment. In the case of a post-synthesis treatment, such as a hydrothermal treatment, this change is accompanied by the creation of a mesoporosity, which is particularly significant in the case of zeolites having a unidirectional structure because this mesoporosity enables the channels in the zeolite to be connected. There is thus an optimum aluminic fraction which is a function of the zeolite and of the reaction under consideration.

ZSM-5, a zeolite discovered by Mobil and having a structure of the MFI type and described in the "Atlas of zeolite structure types" by Meier and Olson (1987 edition, Butterworth), is obtained by direct synthesis with a low aluminic fraction of less than 0.1.

Offretite, the structure of which is described in the same atlas, results from the hydrothermal crystallization of an aluminosilicate gel taken in the system comprising a source of silicon, a source of aluminium, an alkali metal, which is generally potassium, and a structuring agent, which is generally a quaternary ammonium ion such as the tetramethylammonium ion. At the end of the synthesis, the aluminic molar fraction is about 0.2.

In the case of offretite, direct synthesis does not enable the aluminic fraction to be changed in a significant manner. The only route then open for changing this ratio is that of modifying the framework already formed. This route is not without risk, the crystalline structure of offretite being very easily destroyed by these treatments. Thus, the dealumination of offretite by acid treatment for a long time appeared to be impossible, the framework being destroyed by these treatments (F. HERNANDEZ, R. IBARRA, F. FAJULA, F. FIGUERAS, Acta Phys. Chem. 31, 81 (1985)).

A process for the dealumination of offretite has recently been developed by the Institut Francais du Pétrole (French Petroleum Institute). This process, described in European Patent Application 190949, requires numerous calcination, cation exchange, steam treatment and acid attack steps.

The multiplicity of these elementary steps makes industrial implementation of this process uncertain and in any case extremely expensive.

SUMMARY OF THE INVENTION

We have now found a simplified process which enables a crystalline aluminosilicate having the offretite structure and a low aluminic fraction to be obtained in a few steps.

This aluminosilicate has a good selectivity in the acid catalysis reactions and is characterized by its good stability.

Our process for the synthesis of a silica-enriched crystalline aluminosilicate having the offretite structure comprises the following steps:

preparation of a nucleation gel A containing sources of silicon, aluminium, alkali metal ions (M), an organic structuring agent (Z) and water resting this mixture preparation of a growth gel B containing a source of silicon, aluminium, alkali metal ions and water addition of at least 2% by weight of aged gel A to fresh gel B heating the gel A-B with stirring to achieve its crystallization, followed by separation, washing and drying of the crystals calcination at a temperature sufficient to remove the organic structuring agent replacement of the alkali metal ions by protons hydrothermal treatment treatment with a strong mineral acid in an aqueous medium, followed by separation, washing and conditioning of the crystals. Depending on the type of catalytic process, this conditioning can be a calcination, an atomization or, directly, an extrusion in the presence of a binder.

One variant of the process consists in removing the structuring agent at the same time as the potassium ions without passing through a preliminary calcination step.

DESCRIPTION OF THE PREFERRED EMBODIMENTS

The gels A and B contain the same sources of silicon, aluminium and alkali metal but only gel A contains the structuring agent. The stoichiometries can be modified providing they remain within the area of the crystallization of pure offretite, that is to say remain under conditions for which the strain index of the offretite obtained is less than 2.

In order to obtain a pure offretite having a strain index of less than 2, the molar ratios of the reactants in the gels A and B must remain between the following limits:

$SiO_2/Al_2O_3 = 5-40$ $SiO_2/$alkali metal ion$=1-2.6$ structuring agent/alkali metal ion$=0-0.3$ $H_2O/$alkali metal ion$=27-50$ The alkali metal ion used is generally potassium and/or sodium. Potassium is preferably used, in the form of KOH.

Among the organic structuring agents, the tetraalkylammoniums are more commonly used and preferably tetramethylammonium.

The source of silicon can be chosen from silicates, solid silicas, colloidal silicas, silica gels or xerogels or diatomite.

The source of aluminium is in general an aluminium salt, such as sodium aluminate, potassium aluminate, aluminium oxide or aluminium hydroxide.

Natural or synthetic crystalline aluminosilicates, such as kaolin, metakaolinite, perlite or zeolites, can advantageously be used. In this case the silicon/aluminium ratio can be adjusted by a second source of silicon or aluminium. All or part of the mother liquors obtained from a first synthesis can also be used in the preparation of the gel B.

A typical stoichiometry is as follows:

Gel A $6K_2O$, $3(TMA)_2O$, $1Al_2O_3$, $16 SiO_2$, $300H_2O$

Gel b $6K_2O$, $1Al_2O_3$, $16 SiO_2$, $300H_2O$

The nucleation gel A, consisting of sources silicon, aluminium, alkali metal ions, organic structuring agent and water, is left to stand for about 12 to 300 hours at a temperature of between 10° and 100° C., but in general close to ambient temperature. 2 to 50% and preferably 5 to 20% by weight of this aged nucleation gel A are added to the freshly prepared growth gel B.

The mixture A-B crystallizes, under autogenous pressure, with or without stirring, at a temperature of between 20° and 200° C. and preferably between 100° and 150° C. for 2 to 50 and preferably between 8 and 20 hours.

The offretite crystals are separated off, generally by filtration, then washed and dried.

The aim of the calcination step is to remove the organic structuring agent. In general it necessitates heating for 15 minutes to 5 hours at a temperature greater than 500° C.

In general a solution of an ammonium salt, such as ammonium acetate, ammonium sulphate or ammonium nitrate, is used for replacement of the alkali metal ions. Depending on the type of equipment and on the temperature, it is sometimes necessary to carry out several successive replacements. Conventionally the degree of replacement is about 70%, which corresponds to a residual alkali metal ion content of 2 to 3% by weight in the case of potassium.

The hydrothermal treatment takes place at a temperature of between 500° and 850° C. under 100% steam for a period of less than 5 hours. It is possible to carry out the hydrothermal treatment on the non-dried product, in a static atmosphere. In this case the moisture is provided by the product itself (self-steaming).

In general a mineral acid such as nitric acid, sulphuric acid or hydrochloric acid is used for the treatment with a strong mineral acid. By judiciously selecting the concentration and the treatment time as well as the temperature, it is possible to remove aluminic debris without affecting the crystallinity. In general this treatment is carried out under reflux for a period of less than 5 hours.

The aluminosilicate obtained has a strain index of less than 2; the aluminic molar fraction is less than 0.15. These values show that the silica-enriched aluminosilicate obtained, having the offretite structure, has preserved its crystalline structure and its porosity.

The offretite obtained can be used as a pure catalyst, in the form, for example, of powder or grains. It can be advantageous to add an inert binder, such as, for example, alumina, silica, silica/aluminas or clays.

It is also possible to use this offretite in combination with other catalysts, in particular other zeolites, or interchanged for rare earths.

The catalysts obtained can be used for reactions for converting hydrocarbons. We may mention the isomerization of alkanes and alkyl-aromatic compounds such as xylene, the disproportionation of toluene, the alkylation of aromatic rings in the synthesis of ethylbenzene and the conversion of octane to the aromatic compound styrene. They are also suitable for the oligomerization of short-chain olefins for the synthesis of lubricants and paraffin extraction from lubricants or other petroleum fractions containing paraffins. They can also be used for the hydration of olefins. As a FCC catalyst they increase the yield of LPG and the octane index of the petrol obtained.

They are used as catalysts in the synthesis of petrols from methanol or by the Fischer-Tropsch process.

The offretite obtained is also used as a molecular sieve, for example for the separation of the isomers of xylene and of ethylbenzene and drying of organic compounds.

The following examples illustrate the invention without, however, restricting it.

EXAMPLE 1

A nucleation gel A of molar composition $6K_2O, 3(TMA)_2 0.1Al_2O_3, 16 SiO_2, 300 H_2O$ is prepared from 85% potassium hydroxide pellets, metakaolin, silica and a salt containing tetramethylammonium ions.

The mixture is aged with gentle stirring at ambient temperature for 3 days.

A second, growth, gel B having the molar composition $6K_2O, 1Al_2O_3, 16 SiO_2, 300 H_2O$ is obtained from the same constituents as gel A but in the absence of structuring agent.

A mixture consisting of 10% of gel A and 90% by weight of gel B is transferred to a stirred autoclave where it is kept at 150° C. for 12 hours.

The offretite crystals obtained are in the form of hexagonal prisms of regular shapes about 0.5 to 1 n in length and having a length to diameter ratio of 2 to 3.

Examination of these crystals by electron diffraction in a dark field reveals a perfect offretite, while on a conventional sample of offretite the presence of structural defects of the erionite type are detected.

The activation of this zeolite was effected using a commonplace procedure:
- washing to remove the mother liquors
- calcination in air at 550° C. to remove the structuring agent
- replacement by ammoniumsulphate to remove the major proportion of potassium
- hydrothermal treatment at 500° or 800° C. to effect more or less extensive dealumination of the network
- washing with 1 N sulphuric acid under reflux to remove the amorphous debris.

1a) The sample treated at 500° C. has an aluminic molar function of 0.11. Its crystallinity measured by X-rays using the powder method is 100% with respect to calcined offretite. The strain index SI, determined at 350° C. at the end of 20 minutes on an equimolecular mixture of n-hexane and 3-methylpentane, is 1.0.

1b) The sample treated at 800° C. has an aluminic molar fraction of 0.06. Its crystallinity measured by X-rays using the powder method is 95% with respect to calcined offretite. The strain index SI, determined at 350° C. at the end of 20 minutes on an equimolecular mixture of n-hexane and 3-methylpentane, is 1.0.

The catalytic properties of these two offretites are described in the examples below.

EXAMPLE 2

Isomerization of C5–C6 cuts.

A catalyst for the isomerization of straight-chain C5–C6 paraffins was prepared by mechanically mixing a dealuminated offretite having an aluminium molar fraction $m=Al/Al+Si$ of 0.11 (Si/Al=8) with a Pt-on-alumina hydrogenation catalyst (final platinum content 0.5%).

This catalyst was used to isomerize n-pentane at 220° C., 1 atmosphere total pressure, a hydrogen to hydrocarbon ratio of 70 and a space velocity (weight of pentane/weight of zeolites * time in hours) of 0.2 $h^{-1}$.

The conversion obtained was 30% with a selectivity of 100% for isopentane. In the isomerization of n-hexane, using the same operating conditions, the conversion obtained was 45% with a selectivity of 90% for isomers and of 10% for cracking products.

When evaluated under identical operating conditions, a commercial isomerization catalyst based on dealuminated mordenite gave the following results:
- reaction of n-pentane: 16% conversion with a selectivity of 80% for isopentane and 20% for cracking products,
- reaction of n-hexane: 30% conversion with a selectivity of 70% for isomers and 30% for cracking products.

The catalyst based on dealuminated offretite (m=0.11) therefore proved more active and more selective than the reference catalyst based on mordenite for the two reactions.

EXAMPLE 3

Alkylation of benzene by ethanol.

An offretite having a ratio m of 0.11 was tested in the alkylation of benzene by ethanol at 250° C., at 1 atmosphere pressure, a benzene/ethanol ratio of 7 and a space velocity of 4 $h^{-1}$. A rate of conversion of benzene of 3.56 mmoles/g*h was obtained with a selectivity of 92% for ethylbenzene.

Under the same test conditions, an offretite which had not been dealuminated (m=0.28, Si/Al=2.5) gives a rate of 0.3 mmoles/g*h and a selectivity of 30%.

EXAMPLE 4

Conversion of methanol to olefins.

A dealuminated offretite having a ratio m of 0.062 (Si/Al=15) was used to convert methanol to olefins at 370° C., 1 atmosphere pressure, a methanol flow rate of 20 ml/h and a nitrogen flow rate of 9 l/h. The weight of zeolite was 1.5 g. After a reaction time of three hours, the conversion of methanol was 100% and the distribution of the products as follows:

| | |
|---|---|
| Methane | 30.4% |
| Ethane + ethylene | 40.7% |
| Propane | 12.2% |
| Propylene | 11.2% |
| Butane | 1.6% |
| Butenes | 3.9% |

An offretite which had not been dealuminated which was tested under the same conditions led, after a reaction time of 30 minutes, only to 29% of dimethyl ether and is totally inactive after a reaction time of 3 hours.

EXAMPLE 5

Conversion of a mixed charge of ethylbenzene/xylenes.

An offretite having a ratio m of 0.062 is mixed with a platinum-on-alumina hydrogenation catalyst so as to obtain a bifunctional Pt/zeolite catalyst containing 0.3% of Pt. This catalyst is used to convert a charge containing 25% of ethylbenzene and 75% of o-xylene at 380° C., under 10 atmospheres pressure, with a hydrogen/hydrocarbon ratio of 4 and a space velocity of 40 $h^{-1}$. The conversions obtained are 82% for ortho-xylene and 55% for ethylbenzene with a yield of xylenes of 92%.

Under the same reaction conditions, a reference catalyst based on dealuminated mordenite leads to conversions of 70% and 42% for o-xylene and ethylbenzene respectively, with a yield of xylenes of 51%.

EXAMPLE 6

We measured the efficacy of offretite according to the invention as a FCC catalyst using a laboratory method according to the standard ASTM D 3907-87.

The hydrocarbon charge treated is a typical charge taken from a refinery; the characteristics are summarized as follows:

$d_4^{15}=0.922$ aniline point=82.1° C.

viscosity at 100° C.=$6.08 \times 10^{-6} m^2/s$ sulphur=2.68% nitrogen=800 ppm

Conradson carbon=0.44% distillation in accordance with ASTM D-1160

5% 324° C.

10% 361° C.

50% 431° C.

90% 502° C.

95% 519° C.

We used three catalysts, A, B and C:

A=industrial catalyst from the CROSFIELD Company, subjected to a steam treatment at 750° C. for 17 hours under 100% steam.

B=95% of catalyst A+5% of a fresh offretite having an aluminic fraction of 0.11.

C=95% of catalyst A+5% of fresh ZSM-5. This ZSM-5 is identical to that used industrially in catalytic crackers.

Operating conditions=6 grams of catalyst, temperature= 530° C., catalyst/charge ratio=6, injection time=20 seconds, corresponding to a weight/weight/hour of 30 g/g.h.

The results are summarized in Table I.

TABLE I

|   | A (comparative) | B | C (comparative) |
|---|---|---|---|
| $H_2$ | 0.05 | 0.07 | 0.08 |
| $C_1$ | 0.78 | 1.09 | 1.05 |
| $C_2$ | 0.55 | 0.77 | 0.93 |
| $C_2=$ | 1.56 | 2.57 | 3.94 |
| $C_3$ | 2.34 | 5.01 | 5.30 |
| $C_3=$ | 8.05 | 8.52 | 8.36 |
| $iC_4$ | 7.02 | 10.89 | 8.44 |
| $nC_4$ | 1.45 | 2.64 | 2.37 |
| $C_4=$ | 7.34 | 6.10 | 5.49 |
| gas ($H_2 + C_1 + C_2$) | 2.94 | 4.50 | 6.00 |
| LPG ($C_3 + C_4$) | 26.20 | 33.16 | 29.96 |
| petrol ($C_5 - 215$) | 41.58 | 36.32 | 34.58 |
| gas-oil (215–350° C.) | 15.32 | 14.01 | 15.94 |
| residue (350° C.) | 9.56 | 6.90 | 8.58 |
| coke | 4.40 | 5.11 | 4.94 |

The offretite is more selective than the ZSM-5. It enables the quantity of LPG to be increased without too great a loss of petrol yield. Moreover, its better selectivity for isobutane would indicate a greater gain in the octane index and very particularly in the engine octane index.

EXAMPLE 7 (Comparative)

A mixture of stoichiometric composition: 4.46 $K_2O$; 2.56 $TMA_2O$; $Al_2O_3$; 15.3 $SiO_2$; 280 $H_2O$ is prepared by dissolving 0.73 g of metakaolin in a solution containing 15 ml of water, 1.65 g of potassium hydroxide in pellets (KOH) and 3.05 g of tetramethylammonium hydroxide pentahydrate (TMAOH, $5H_2O$ ). After mixing these ingredients, 2.63 g of silica (silica gel in grains) are added.

The whole is crystallized at 110° C. for 72 hours to produce an offretite, which is well crystallized according to its X-ray diffractogram and which has the following chemical composition:

0.79 $K_2O$; 0.20 $TMA_2O$; $Al_2O_3$; 7.1 $SiO_2$; 7.2 $H_2O$.

This solid is converted to a zeolite with ammonium replacement by i) calcination at 500° C. in air for 4 hours and ii) exchange under reflux in a 1 N solution of $NH_4NO_3$ for 10 hours with a liquid/solid ratio of 100/l. The solid in which the replacement has been made has retained its crystallinity, evaluated by X-ray diffraction, and its alkali metal ion content is 1.3% by weight.

This solid was dealuminated by hydrothermal treatment in a confined atmosphere (self-steaming) at a temperature of 650° C. for 2 hours.

After dealumination, its crystallinity, evaluated by X-ray diffraction, corresponds only to 30% of the crystallinity of the initial solid and its porosity is not accessible to molecules as small as nitrogen since its pore volume measured by the techniques well known in the art is less than 0.01 ml absorbed per gram of zeolite.

The acid attack carried out on the dealuminated solid in order to liberate the porosity was effected under the following conditions:

50 ml of 0.5 N HCl per gramme of zeolite ambient temperature reaction time of 4 hours Despite the mild conditions, the solid is entirely amorphous after acid attack.

This example shows that dealuminated offretite obtained by a conventional synthesis followed by a simple dealumination loses its crystallinity and its porosity.

We claim:

1. Process for the synthesis of dealuminated offretite, which comprises the following steps:

preparation of a nucleation gel A containing sources of silicon, aluminum, alkali metal ions (M), an organic structuring agent (Z) and water aging this mixture preparation of a growth gel B containing a source of silicon, aluminum, alkali metal ions and water addition of at least 2% by weight of aged gel A to fresh gel B heating the gel A-B with stirring to achieve its crystallization, followed by separation, washing and drying of the crystals calcination at a temperature greater than about 500° C. to remove organic structuring agent replacement of the alkali metal ions by protons hydrothermal treatment with 100% steam at a temperature between about 500° to 800° C. for a period of less than 5 hours treatment with a strong mineral acid in an aqueous medium, followed by separation, washing and conditioning of the crystals.

2. Process according to claim 1, wherein the molar ratios in the gels A and B are between the following limits:

$SiO_2/Al_2O_3$=5–40

$SiO_2$/alkali metal ion=1–2.6 structuring agent/alkali metal ion=0–0.3

$H_2O$/alkali metal ion=27–50

3. Process according to claims 1, wherein the alkali metal ion is potassium and/or sodium.

4. Process according to claim 1 wherein the organic structuring agent is a tetraalkylammonium.

5. Process according to claim 1 wherein the source of silicon is selected from the group consisting of silicates, solid silicas, colloidal silicas, silica gels, xerogels and diatomite.

6. Process according to claim 1 wherein the source of aluminium is an aluminium salt, of the group consisting of sodium aluminate, potassium aluminate, aluminium oxide, aluminium hydroxide and a natural or synthetic crystalline aluminosilicate.

7. Process according to claim 1 wherein the nucleation gel A is left to stand for 12 to 300 hours at a temperature of between 10° and 100° C.

8. Process according to claim 1 wherein 2 to 50% by weight of aged gel A are added to fresh gel B.

9. Process according to claim 1 wherein the mixture A-B crystallizes, under autogenous pressure, at a temperature of between 20° and 200° C. for 2 to 50 hours and the crystals are then separated off, washed and dried.

10. Process according to claim 1 wherein the organic structuring agent is removed by heating for 15 minutes to 5 hours at a temperature greater than 500° C.

11. Process according to claim 1 wherein the alkali metal ions are replaced by a solution of an ammonium salt, of the group consisting of ammonium acetate, ammonium sulphate and ammonium nitrate.

12. Process according to claim 1 wherein the hydrothermal treatment takes place at a temperature of between 500° and 850° C. under 100% steam for a period of less than 5 hours.

13. Process according to claim 12, characterized in that the steam originates from the non-dried product.

14. Process according to claim 1 wherein the strong mineral acid used for the acid treatment is of the group consisting of nitric acid, sulphuric acid and hydrochloric acid.

15. Process according to claim 1 wherein the acid treatment is carried out by heating under reflux for a period of less than 5 hours.

16. Process according to claim 1 wherein the mixture A-B crystallizes, under autogenous pressure, at a temperature of between 100° and 150° C. for 8 to 20 hours and the crystals are then separated off, washed and dried.

17. Process according to claim 1 or 2, wherein the source of alkali metal ion is KOH.

18. Process according to claim 4, wherein the organic structuring agent is tetramethylammonium.

19. Process according to claim 1, wherein 5 to 20% by weight of aged gel A are added to fresh gel B.

20. Silica-enriched crystalline aluminosilicate having the offretite structure prepared by the process of claim 1, and having a strain index of less than 2 and an aluminium molar fraction (m) as determined by the formula $$m = \frac{Al}{Al + Si}$$

of less than 0.15.

21. A process for the synthesis of dealuminated offretite without a major loss of crystallinity and which utilizes a treatment with a strong mineral acid, which process comprising the steps of:

(1) preparing a nucleation gel A comprised of a mixture containing sources of silicon, aluminium, alkali metal ions (M), and an organic structuring agent (Z) and water, (2) allowing the mixture to age for a period of at least about 12 hours, (3) preparing a growth gel B comprised of a mixture containing a source of silicon, aluminium, alkali meal ions and water, (4) adding at least 2% by weight of aged gel A to fresh gel B to form a gel A-B mixture, (5) heating the gel A-B mixture with stirring to achieve crystallization, followed by separation, washing and drying of the crystals, (6) calcining said crystals at a temperature greater than about 500° C. sufficient to remove the organic structuring agent, (7) replacing the alkali metal ions in said crystals by protons, (8) subjecting said crystals to hydrothermal treatment with 100% steam at a temperature of between about 500° and 800° C. for a period of less than 5 hours, and (9) treating said crystals with a strong mineral acid in an aqueous medium, followed by separation, washing and conditioning of the crystals.

22. A catalyst for the conversion of hydrocarbons comprised of a silica-enriched crystalline aluminosilicate having the offretite structure prepared by the process of claim 21.

* * * * *